US00PP32346P2

(12) United States Plant Patent
Olesen

(10) Patent No.: US PP32,346 P2
(45) Date of Patent: Oct. 20, 2020

(54) COMPACT FLORIBUNDA ROSE PLANT NAMED 'POULCAS061'

(50) Latin Name: ***Rosa* hybrid**
Varietal Denomination: Poulcas061

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,247

(22) Filed: Sep. 4, 2019

(51) Int. Cl.
*A01H 5/02* (2018.01)
*A01H 6/74* (2018.01)

(52) U.S. Cl.
USPC ..... Plt./141

(58) Field of Classification Search
USPC ..... Plt./141
See application file for complete search history.

(56) References Cited

PUBLICATIONS http://www.poulsenroser.com/assortment/rose-collections/castle/mendoza.aspx.2020.*
PLUTO Plant Variety Database Mar. 6, 2020. p. 1.*

* cited by examiner

*Primary Examiner* — Annette H Para

(57) ABSTRACT

A new garden rose plant of the Compact Floribunda class which has abundant, red purple flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas061'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulcas061', originated as a single seedling from the stated cross.

The new variety may be distinguished from its male pollen parent and female seed parent primarily by the following characteristics. The male pollen parent plant has ivory white flowers while the new variety has red purple flowers. The female seed parent plant has lavender flowers while the new variety has red purple flowers.

The objective of the hybridization of this rose variety was to create a new and distinct variety with unique qualities, such as:

1. Uniform and abundant red purple flowers;
2. Vigorous, but compact growth when propagated on its own roots;
3. Exceptional disease resistance.

This combination of qualities is not present in previously available commercial cultivars of this type, known to the inventor, and distinguish 'Poulcas061' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulcas061' was selected in the spring of 2011 by the inventor as a single plant from the progeny of the aforementioned hybridization.

Asexual reproduction of 'Poulcas061' by rooted cuttings was first done by Mogens N. Olesen in the nursery in Fredensborg, Denmark in July, 2011. This initial and other subsequent asexual propagations conducted in controlled environments have demonstrated that the characteristics of 'Poulcas061' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas061'.

Specifically illustrated in FIG. 1 of the drawings are open flowers, petals detached, sepals detached showing reproductive flower parts, leaf, and bare stem.

Figure 1:
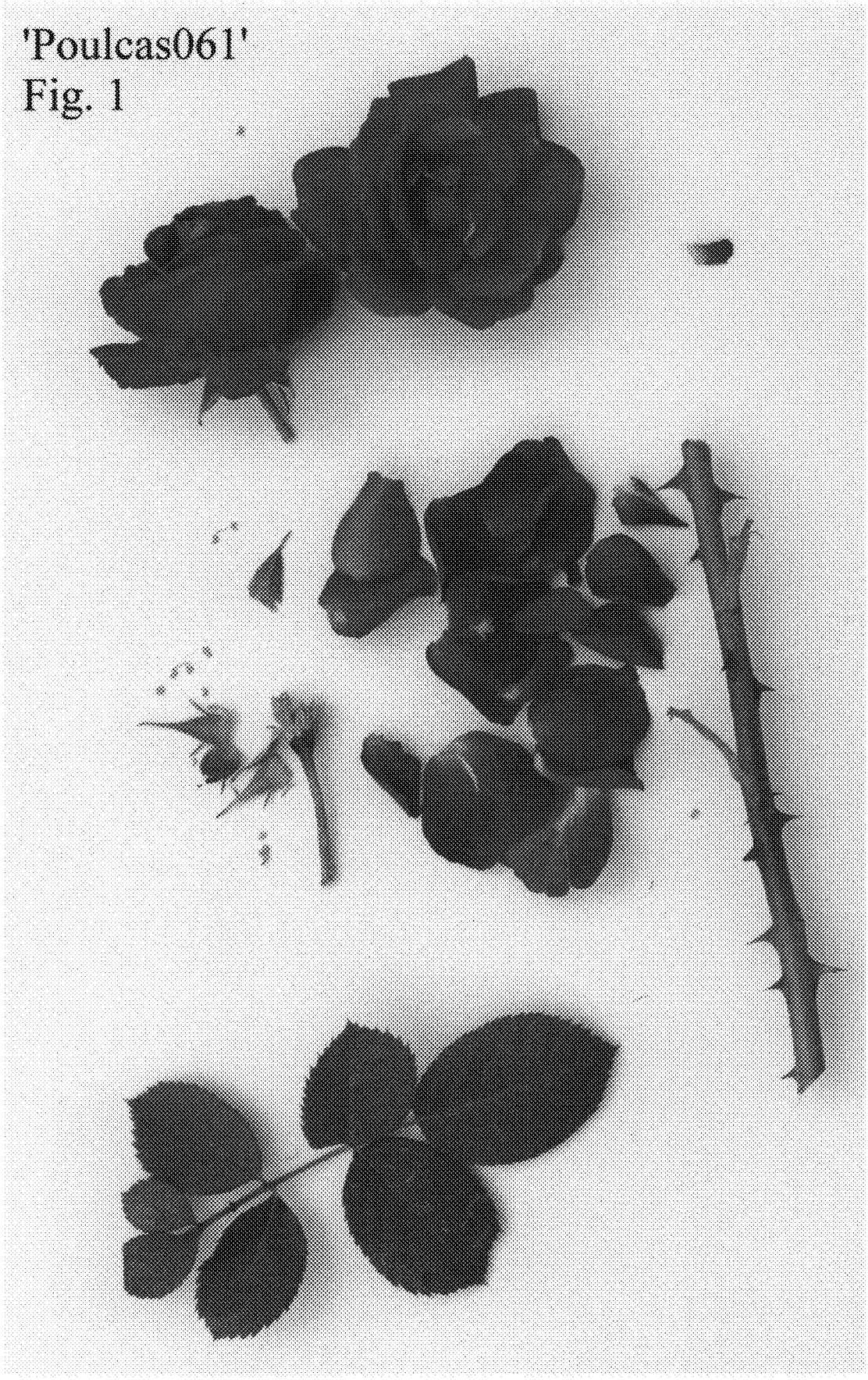
Figure 2:
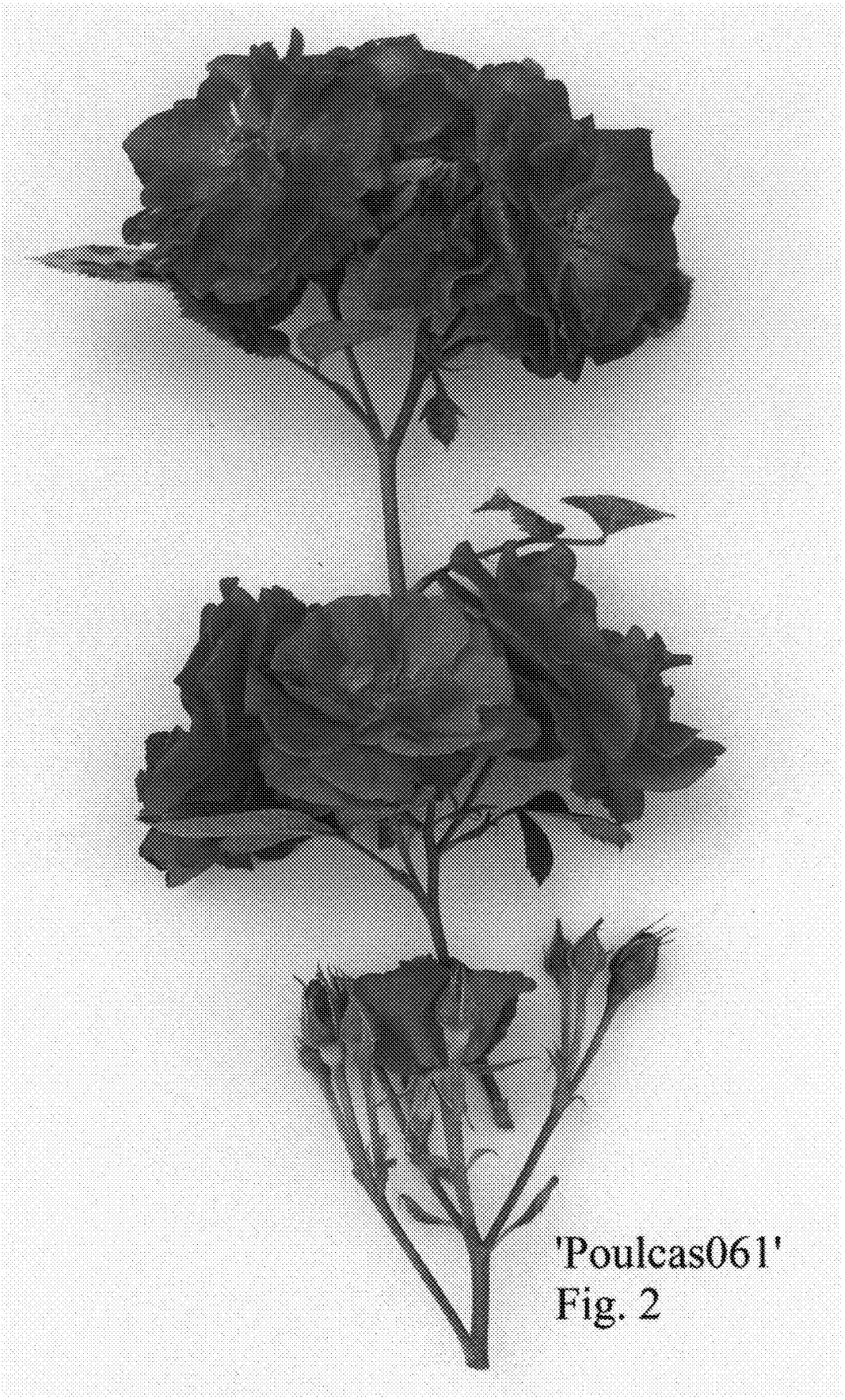

Specifically illustrated in FIG. 2 of the drawings are clusters of flowers on the branch, at various stages of opening. Plants shown are 2 years of age.

DETAILED DESCRIPTION OF THE VARIETY

The following is a description of 'Poulcas061', as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpal063', U.S. Plant Pat. No. 24,635 are compared to 'Poulcas061' in Chart 1.

CHART 1

| | 'Poulcas061' | 'Poulpal063' |
|---|---|---|
| Petal Count | 35-40 petals | 65 petals |
| Flower Diameter | 80 mm | 80 to 90 mm |
| General Tonality of Flower Color | Red-Purple Group 71B with shades of Red-Purple Group 71A | Red-Purple Group 58C |

FLOWER AND FLOWER BUD

Blooming habit: Continuous.

Flower bud:

*Size.*—Upon opening, 26 mm in length from base of receptacle to end of bud. Bud diameter is 14 mm.

*Bud form.*—Ovoid.

*Bud color.*—As sepals divide petals are Red-Purple Group 67A.

*Sepal inner surface.*—Color: Yellow-Green Group 144B. Surface: Lightly pubescent.

*Sepal outer surface.*—Color: Yellow-Green Group 144A with intonations of Greyed-Red Group 179A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—20 mm long, 9 mm wide.

*Receptacle.*—Texture: Smooth. Size: 8 mm in height, 6 mm wide. Color: Yellow-Green Group 144A with intonations of Greyed-Orange Group 166B. Shape: Campanulate.

*Pedicel.*—Surface: Smooth. Length: 35 mm. Diameter: 3 mm on average. Color: Yellow-Green Group 144B with intonations of Greyed-Orange Group 166B. Strength: Strong.

*Peduncle.*—Length: 6 to 10 cm. Diameter: About 4 mm. Color: Yellow-Green Group 145A. Texture: Smooth.

Flower bud development: Flower buds are borne in clusters of 15 to 25 flower buds per stem.

Flower bloom:

*Fragrance.*—Strong perfume.

*Duration.*—The blooms have a duration on the plant of approximately 10 days. Petals fall cleanly away from plant after flowers have fully matured.

*Size.*—Flower diameter is 80 mm when open. Flower depth is 35 mm.

*Flower shape.*—High centered double, with reflexed petals and a slightly high pointed center.

*Shape of flower, side view.*—The upper portion is convex. The lower portion is concave.

Petalage: Under normal conditions, flowers have about 35-40 petals.

General tonality of flower: Open flowers are Red-Purple Group 71B with shades of Red-Purple Group 71A.

Petal color:

*Upon opening, petals.*—Upper surface: Red-Purple Group 71A. Lower surface: Red-Purple Group 64A.

*Basal petal spots, upon opening.*—Upper surface: Yellow Group 2A. Lower surface: Yellow Group 2A.

*After opening, petals.*—Upper surface: Red-Purple Group 71A. Lower surface: Red-Purple Group 64A.

*Basal petal spots, after opening.*—Upper surface: Yellow Group 2A. Lower surface: Yellow Group 2A.

Petals:

*Petal reflex.*—Moderate to strong.

*Margin.*—Entire and uniform. Moderate undulations.

*Shape.*—Broad and elliptic. Apex shape: Rounded. Base shape: Acute.

*Size.*—35 mm (l)×37 mm (w).

*Texture.*—Smooth.

*Thickness.*—Average.

Petaloids:

*Size.*—10 mm (l) by 4 to 8 mm (w).

*Quantity.*—About 6.

*Shape.*—Elliptical with an acute base and rounded apices.

*Color.*—Red-Purple Group 71A above, Red-Purple Group 64A underneath.

Reproductive flower parts:

*Pollen.*—None observed.

*Anthers.*—Size: 2 mm in length. Color: Greyed-Orange Group N167A. Quantity: 35 on average.

*Filaments.*—Color: Yellow Group 8C. Length: 10 mm.

*Pistils.*—Length: 6 mm. Quantity: 35 on average.

*Stigmas.*—Color: Green-White Group 157A.

*Styles.*—Color: Green-White Group 157A.

*Location of stigmas.*—Inferior in location relative to the length of the filaments and the height of the anthers.

*Hips.*—None Observed.

PLANT

Plant growth: Upright. Plants are about 95 cm in height, and 85 cm wide.

Stems:

*Color of juvenile growth.*—Yellow-Green Group 144A with intonations of Greyed-Orange Group 176A.

*Color of mature growth.*—Yellow-Green Group 144A.

*Length.*—Canes are about 40 cm from the base of the plant to the flowering portion.

*Diameter.*—About 8 mm.

*Internodes.*—On mature canes about 44 mm between nodes.

*Surface texture.*—Young wood: Smooth. Older wood: Smooth.

Long prickles:

*Incidence.*—11 prickles per 10 cm of stem.

*Size.*—Average length of prickles on mature stems is 9 mm.

*Shape.*—Upper portion is linear. Lower portion is concave.

*Color.*—Juvenile prickles: Greyed-Red Group 178B. Mature prickles: Greyed-Red Group 178B.

Plant foliage:

*Compound leaf.*—155 mm (l)×110 mm (w).

*Quantity.*—2 leaves per 10 cm of stem on average.

*Leaf bearing angle to the stem.*—45 degrees.

*Color of juvenile foliage.*—Upper side: Yellow-Green Group 144A. Lower side: Yellow-Green Group 144B.

*Color of mature foliage*.—Upper side: Yellow-Green Group 146A. Lower side: Yellow-Green Group 147C.

Plant leaves and leaflets.—

*Stipules*.—Size: 8 mm long, mm wide. Quantity: 2 per compound leaf. Shape: Linear, slightly broad based with outward extending apices. Margins: Finely serrated. Color: Yellow-Green Group 144A.

*Petiole*.—Length: About 33 mm. Diameter: About 2.5 mm. Upper surface color: Yellow-Green Group 144A. Lower surface color: Yellow-Green Group 144A.

*Rachis*.—Length: 65 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 60 mm long, 40 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulcas061', substantially as illustrated and described herein, due to its abundant red purple flowers, disease resistance, and extended period of bloom.

* * * * *

'Poulcas061'

'Poulcas061'